(12) United States Patent
Hall et al.

(10) Patent No.: US 7,583,828 B2
(45) Date of Patent: Sep. 1, 2009

(54) ACCUMULATION IMAGING

(75) Inventors: Anne Lindsay Hall, New Berlin, WI (US); Michael Joseph Washburn, Bookfield, WI (US); Koji Miyama, Hachiouji (JP); Kirstin Nora LaConte, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 580 days.

(21) Appl. No.: 10/920,813

(22) Filed: Aug. 18, 2004

(65) Prior Publication Data

US 2006/0039589 A1 Feb. 23, 2006

(51) Int. Cl.
*G06K 9/00* (2006.01)
*A61B 8/00* (2006.01)

(52) U.S. Cl. .................................. 382/128; 600/443
(58) Field of Classification Search ................. 382/128; 600/443, 438
See application file for complete search history.

(56) References Cited

U.S. PATENT DOCUMENTS 5,099,847 A * 3/1992 Powers et al. ............... 600/443
6,056,691 A * 5/2000 Urbano et al. .............. 600/443
6,144,758 A * 11/2000 Fukushima et al. ......... 382/128
6,373,970 B1 * 4/2002 Dong et al. ................. 382/128
6,967,675 B1 * 11/2005 Ito et al. .................. 348/207.1
2003/0222980 A1 * 12/2003 Miyagaki et al. ............ 348/115
2004/0172292 A1 * 9/2004 Takekoshi et al. .............. 705/2

* cited by examiner

*Primary Examiner*—John B Strege
(74) *Attorney, Agent, or Firm*—McAndrews, Held & Malloy, Ltd.; Peter J. Vogel; Michael A. Dellapenna

(57) ABSTRACT

A system for displaying accumulated ultrasound images of tissue structures. A set of N image frames is used to produce a peak image display. Multiple peak image displays are produced by discarding the oldest image frame in the set of N image frames and replacing the discarded image frame with another more recent image frame. The more recent image frame is added to the set of image frames to produce a new set of N image frames. The new set of N image frames is used to produce another peak display image. If there is an undesirable amount of distortion or blur in the peak display images due to tissue motion, then the number of image frames in the set of N image frames can be reduced.

18 Claims, 2 Drawing Sheets

ACCUMULATION IMAGING

BACKGROUND OF THE INVENTION

The present invention generally relates to ultrasound imaging of anatomical structures. In particular, the invention relates to a method and system for improving the display of ultrasound imaging of anatomical structures.

For a number of years, ultrasound imaging has been used to non-invasively monitor and image anatomical structures within the human body. To produce the image, an ultrasonic transducer transmits an ultrasonic wave of energy into a patient's body. The properties of ultrasonic echoes returning from various structures and elements within the patient's body are then used to produce frames of data referred to as image frames. As the image frames are acquired, they may be displayed on a monitor, output to a printer, and/or stored in a memory for playback at a later time.

The human body is not an immobile object. Patient's breathe, blood flows, and tissues move. Because tissues within the patient move during the course of an ultrasound procedure, corresponding tissue structures in successive image frames may appear in different portions of the image frames. Combining data from successive image frames where corresponding tissue structures are misaligned blurs the boundaries between tissue structures and reduces the overall quality of the combined image.

For example, ultrasound is sometimes used to track the flow of fluids in a patient's body. To highlight the flow of fluids in the patient's body, the patient is sometimes injected with a contrast agent, the progression of which is tracked using the ultrasound system. Shortly after the contrast agent is injected, the ultrasound system starts acquiring images, oftentimes set up to scan in special imaging modes designed to preferentially image contrast agents. As the contrast agent flows through the patient's body, successive image frames are continuously acquired.

To display the entire path traversed by a contrast agent as it progresses through the body, a peak display image may be produced that shows the maximum concentration of contrast agent at various points in the body during acquisition of the image frames. To produce the peak display image, a first image frame is acquired. A second image frame is acquired and each pixel of the second image frame is compared with each pixel of the first image frame. The highest value for each pixel amongst the second image frame and the first image frame is used to create a peak display image. Next, a third image frame is obtained and each pixel in the third image frame is compared with corresponding pixels of the peak display image. Pixel intensity values in the third image frame that exceed corresponding pixel values in the peak display image replace the corresponding pixel value in the peak display image to produce an updated peak display image. The process is repeated for each subsequently acquired image frame such that each time a pixel value in a recently acquired image frame exceeds a corresponding pixel value in the peak display image, the pixel value in the recently acquired image frame replaces the corresponding pixel value in the peak display image. Consequently, a running tally is kept of the entire path traversed by contrast agent from the acquisition of the first image frame all the way to the currently acquired image frame.

However, as the successive image frames are acquired, tissues within the patient are moving and corresponding tissue structures in the successive image frames are represented by different pixels. Because the corresponding tissue structures are represented by different pixels in successive image frames, comparing and combining images with misaligned tissue structures pixel to pixel reduces the quality of the combined image. The quality of the image is reduced because misaligned tissue structures in images being compared can result in pixels for body anatomy such as a vein being compared with pixels for a strong reflector such as a tendon resulting in peak values for the tendon possibly replacing values for the vein in the peak display image. Consequently, such misalignment of corresponding tissue structures in successive image frames can blur the boundaries between tissue structures, such as the vein and the tendon, in the peak display image. As a result, prior art systems are susceptible to motion artifacts and blurring because a significant amount of tissue motion can occur during the course of an entire ultrasound procedure.

While an example using contrast agent imaging and a peak display image has been presented, misalignment of corresponding tissue structures is a problem for other ultrasound imaging modes as well. For example, misalignment of corresponding tissue structures effects color flow imaging and B flow imaging.

One solution for reducing the effects of tissue motion on a combined image includes spatial correlation measures. With spatial correlation measures, each image frame is processed and compared with other prior and subsequent image frames to correlate pixels in an image frame with pixels representing the same tissue in prior and subsequent image frames. Due to the sheer number of pixels, comparisons, and correlations, re-aligning corresponding tissue structures using spatial correlation measures requires substantial time and software processing. Delays in image processing due to processing time reduce patient throughput and waste valuable technician time.

Consequently, a need exists for a system that allows for the creation of an accurate peak display image with a reduction in the effects of tissue motion on image quality and accuracy. Additionally, a need exists for a system that reduces the effects of tissue motion without using spatial correlation measures that require substantial time and software processing.

BRIEF SUMMARY OF THE INVENTION

A preferred embodiment of the present invention provides a system for improving the display of ultrasound imaging of tissue structures. A set of N image frames is used to produce a peak image display. Multiple peak image displays are produced by discarding the oldest image frame in the set of N image frames and replacing the discarded image frame with another more recent image frame. The more recent image frame is added to the set of image frames to produce a new set of N image frames. The new set of N image frames is used to produce another peak display image. If there is an undesirable amount of distortion or blur in the peak display images due to tissue motion, then the number of image frames in the set of N image frames can be reduced.

To enhance diagnosis and reduce viewing time, peak display images can be displayed in a split screen mode with other ultrasound images. For example, a peak display image can be displayed in a first portion of the monitor while a real time image is displayed in a second portion of the monitor. Using the split screen mode in this manner allows a medical technician to see a contrast agent as it is flowing through a patient alongside an image that shows the path traveled by the contrast agent.

DETAILED DESCRIPTION OF THE INVENTION

Figure 1:
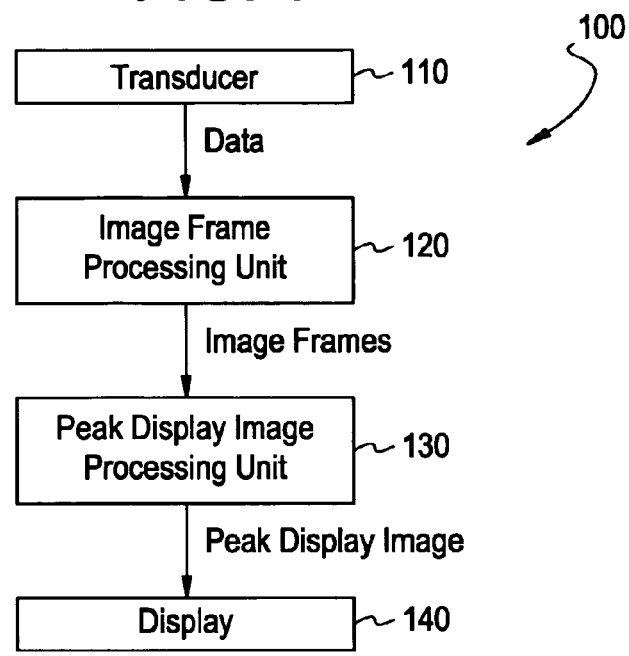
FIG. 1 illustrates a system for reducing the effects of tissue motion on a peak display image in accordance with an embodiment of the present invention.

FIG. 1 illustrates a system 100 for reducing the effects of tissue motion on a peak display image in accordance with an embodiment of the present invention. The system 100 includes a transducer 110, an image frame processing unit 120, a peak display image processing unit 130, and a display 140. The transducer 110 transmits data to the image frame processing unit 120. The image frame processing unit 120 processes the data into ultrasound image frames and transmits the image frames to the peak display image processing unit 130. The peak display image processing unit 130 processes the image frames into a peak display image and transmits the peak display image to the display 140. The display 140 displays the peak display image on a monitor.

Figure 2:
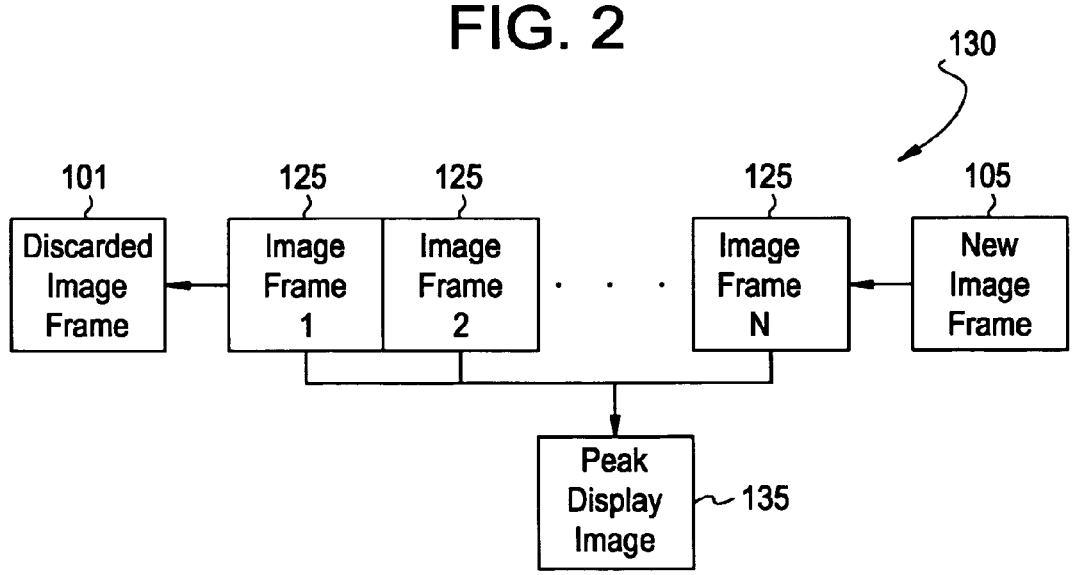
FIG. 2 is a block diagram that illustrates operation of the peak display image processing unit of FIG. 1 in accordance with an embodiment of the present invention.

FIG. 2 is a block diagram that illustrates operation of the peak display image processing unit 130 of FIG. 1 in accordance with an embodiment of the present invention. The peak display image processing unit 130 receives a predetermined number, N, of ultrasound image frames from the image frame processing unit 120. Data from the N image frames is combined to produce a peak display image 135. The peak display image 135 is then transmitted to the display 140.

After a peak display image has been produced, the oldest image frame is discarded and a new image frame is acquired from the image frame processing unit 120 to form a new set of N image frames. Again, data from the set of N image frames, that now includes the new image frame, is combined to produce a peak display image 135. The peak display image 135 is transmitted to the display 140. The process of discarding the oldest image frame, acquiring a new image frame, and calculating a peak display image 135 is repeated as desired.

For example, a set of thirty image frames may initially be acquired from an image frame processing unit. The thirty image frames are compared with one another to determine the peak pixel value for corresponding points amongst the thirty image frames. More specifically, if each of the thirty image frames has five pixels numbered 1 to 5, then each of the five pixels of every image frame is compared with corresponding pixels from every other image frame to determine a peak value for each of the five pixel positions. As an example, pixel 1 of image frame one is compared with pixel 1 of image frames two through thirty. Of the thirty image frames, the highest value for pixel 1 is selected and placed in the pixel 1 position of the peak display image. The process is repeated for all of the remaining pixels 2 through 5.

While only five pixels per image frame were used for the sake of using a simplistic explanation in this example, systems with any number of pixels per image frame can be used. For example, some modern systems use a matrix of 512 by 512 pixels in which each of the more than 250,000 pixels in each image frame would be compared to corresponding pixels in the other image frames to produce a peak display image.

The peak pixel values are used to produce a combined image with each pixel in the combined image representing the peak value for a corresponding pixel amongst the image frames received from the image frame processing unit. Because the combined image includes peak values from the original input ultrasound image frames, it is designated as the peak display image. The peak display image is then transmitted to the display where it is displayed on a monitor.

If there is significant tissue motion amongst the image frames used to create the peak display image, then boundaries between tissue structures in the peak display image may be blurred because corresponding tissue structures may not be represented by the same pixels in the various image frames. To reduce the amount of boundary blurring in the peak display image, the number of image frames used to create the peak display image can be reduced. Reducing the number of image frames used in the peak display image, can reduce the overall range of movement of tissue in the image frames used to create the peak display image. Consequently, the amount of blurring can be reduced by reducing the number of image frames used.

For example, if there is significant tissue movement when thirty image frames are used, then the number of image frames used in creating the peak display image may be reduced to fifteen. By reducing the number of image frames from thirty to fifteen, the period of time spanned by the initial input image frames is reduced. In turn, reducing the period of time spanned by the input image frames reduces the amount of time for movement of tissue structures. Thus, blurring and other image artifacts caused by tissue motion can be reduced.

In an alternative embodiment, a user may input a period of time rather than a number of image frames for the system to use in determining how many frames to use for each peak display image output. For example, a user may instruct the system to produce peak image displays from images spanning three second periods of time. The system will then use this time and the original imaging frame rate to determine the number of image frames to use in producing the peak display images. For example, with a time period of three seconds and a frame rate of thirty image frames per second, then the number of image frames used to create a peak display image would be three seconds times thirty image frames per second which equals ninety frames.

If the amount of movement in the peak display images is undesirable, the period of time may be reduced. For example, the user may instruct the system to produce peak display images spanning a two second period of time rather than a three second period of time if significant movement is detected. With the same thirty frames per second frame rate used above, the number of frames used to create a peak display image would be two seconds times thirty image frames per second which equals sixty. With the number of image frames reduced from ninety to sixty, the range of tissue motion and resulting blurring can be reduced by reducing the time period over which the image frames span; thus, allowing less time for tissue movement.

Figure 3:
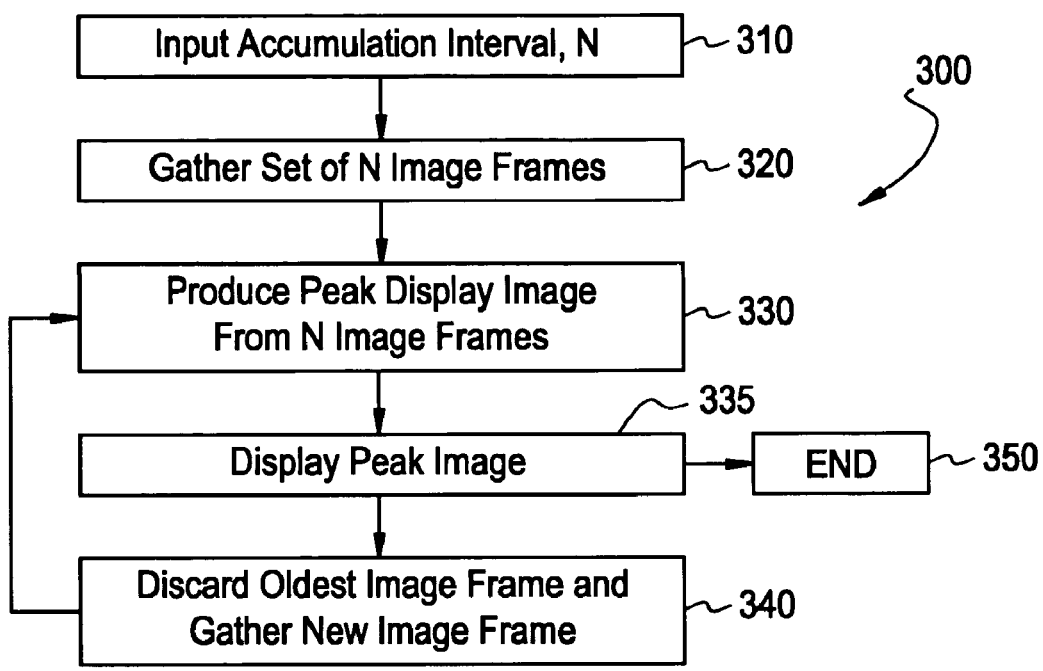
FIG. 3 is a block diagram illustrating a method for producing a peak display image in accordance with an embodiment of the present invention.

FIG. 3 is a block diagram illustrating a method 300 for producing a peak display image in accordance with an embodiment of the present invention. In step 310, a user inputs an accumulation interval N. The accumulation interval N is the number of image frames to be used in producing a peak display image. In an alternative embodiment, the accumulation interval can be a time period that is converted to a number N as described above, representing the number of image frames used in producing the peak display image.

In step 320, a set of image frames 1 to N is gathered. The set of 1 to N image frames can be downloaded from storage in a memory or acquired in real time as the image frames are acquired by ultrasound equipment. The image frames in the set of 1 to N image frames are temporally related with image frame 1 being the oldest image frame in the set and the last image frame N being the most recently acquired image frame in the set.

In step 330, the image frames 1 to N are combined to produce a peak display image. To produce the peak display image, each pixel in the 1 to N image frames is compared with its corresponding pixel in all the other image frames. The peak intensity value for each corresponding pixel in the 1 to N images frames is used for the peak display image. In step 335, the peak display image is then displayed on a display. If another peak display image is desired, then the method proceeds to step 340. If another peak display image is not desired, then the method proceeds to step 350 and ends.

In step 340, the oldest image frame is discarded and another image frame is gathered and added to create a new set of N image frames. The method then proceeds to step 330 and repeats the step of producing a peak display image using the new set of N image frames.

For example, a user may desire to have a peak display image created using the nine most recent image frames. The nine most recent image frames, numbers 1 to 9, may be downloaded from storage in a memory or gathered in real time from the ultrasound equipment and temporarily stored in a memory used for calculating a peak display image. Image frames 1 to 9 are then combined to produce a first peak display image. A peak pixel value for each corresponding pixel in frames 1 to 9 is selected and placed in a first peak display image which is then displayed on an image monitor.

After the first peak display image has been displayed, a new image frame, number 10, is acquired. The oldest image frame, number 1, is discarded. Image frames 2 through 10 are then used to produce a second peak display image which replaces the first peak display image on the image monitor.

After the second peak display image has been displayed, a new image frame, number 11, is acquired. The oldest image frame, number 2, is discarded. Image frames 3 through 11 are used to produce a third peak display image which is then displayed. The process is repeated until the user turns off the accumulation imaging mode, at which point the system returns to scanning without calculating and displaying peak display images.

Thus, peak display images can be continuously created from a set of N image frames by acquiring a new image frame and discarding the oldest image frame in the set of N images. By creating peak display images using a variable accumulation interval such as N, the effects of tissue motion on a peak display image can be reduced without using time intensive spatial correlation techniques. Instead of having to compare every image frame acquired with prior and subsequent image frames and determining which pixels in every image correspond with pixels in every other image, a subset of the image frames can be used that spans a small enough time interval that the amount of tissue motion is considerably reduced.

In the alternative, more than one image frame may be discarded and one image frame then added to a set of N images each time a peak display image is produced. If the motion frame-to-frame is high and exceeds a threshold, then more than one frame may be discarded to reduce the effects of motion on the peak display image. For example, rather than discarding just the oldest image frame, the system can discard the oldest two image frames and then add one new image frame to the set of N image frames, effectively shortening the time period over which the peak display image is calculated.

Also, rather than rely upon user input to adjust the number of frames discarded and added each time a peak display image is produced, the system can be programmed to automatically vary the number of image frames discarded and added. The system can be programmed to detect motion and, if the detected motion is larger than a threshold, increase the number of frames discarded. By increasing the number of discarded frames and maintaining the number of acquired frames constant, the time interval over which the peak display image spans is reduced. The frame-to-frame motion can be determined by a variety of techniques including a simple sum of differences at each pixel location or pixel area. The differences can be compared to any number of thresholds where each threshold indicates the number of frames to discard. After the level of detected motion reduces below a threshold, the system can revert back to using the value of N originally input by the user to construct peak display images.

Figure 4:
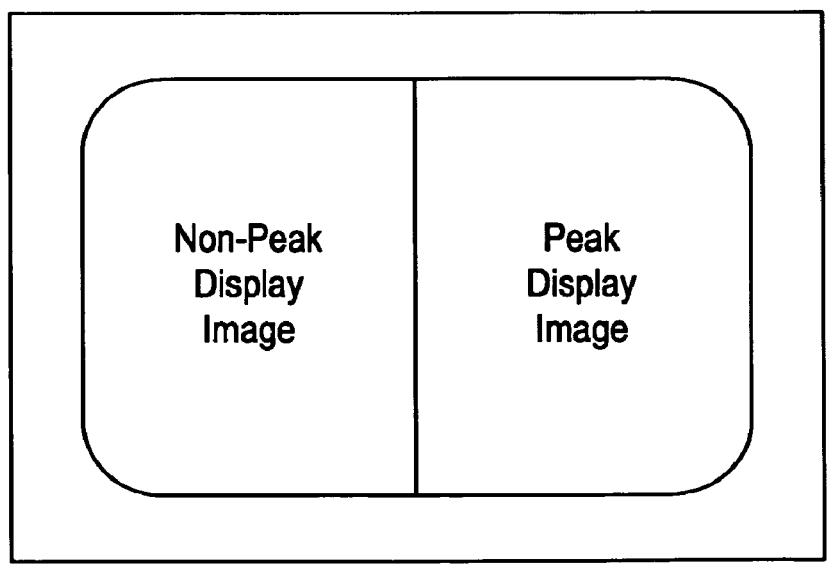
FIG. 4 illustrates a split screen display mode in accordance with an embodiment of the present invention.

In another embodiment of the present invention shown in FIG. 4, the peak display image can be produced using the systems and methods presented above and displayed in a split screen mode with a non-peak display image on the same monitor. For example, as image frames are acquired, the real time image can be displayed on a first portion of a monitor screen and the peak display image can be displayed on a second portion of the monitor screen. Using the split screen mode, a user can see both the true temporal dynamics of the real time image along with the peak display images being produced.

Creating peak display images using sets of image frames rather than continuously comparing an existing peak display image with each individual incoming image frame allows for peak display images to be created after all of the image frames have been acquired for a particular patient. Acquired image frames can be stored in a memory connected to an ultrasound system and/or processed on a separate workstation to which the image frames can be downloaded after acquisition.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

What is claimed is:

1. A method for producing a combined peak display image with reduced distortion due to motion of anatomical structures comprising:
   determining a number of ultrasound image frames to be used in constructing said combined peak display image;
   collecting ultrasound image frames, until said number of image frames has been collected, each of said image frames having a matrix of pixels;
   selecting a peak intensity value for each corresponding pixel from amongst said image frames;
   constructing said combined peak display image with said peak intensity value for each corresponding pixel from amongst said image frames; and
   displaying said combined peak display image on a monitor.

2. The method of claim 1 wherein the step of determining said number of ultrasound image frames to be used in constructing said combined peak display image further comprises inputting said number of image frames.

3. The method of claim 1 wherein the step of determining said number of ultrasound image frames to be used in constructing said combined peak display image further comprises inputting a time period over which successive image frames span.

4. The method of claim 3 wherein the step of determining said number of image frames to be used in constructing said combined peak display image further comprises converting said time period to said number of ultrasound image frames.

5. The method of claim 4 wherein said converting step further comprises multiplying said time period by a frame rate to determine said number of image frames used in constructing said combined peak display image.

6. The method of claim 1 further comprising discarding one of said image frames after constructing said combined peak display image, collecting an additional image frame, and constructing a second combined peak display image.

7. The method of claim 6 wherein constructing said second combined peak display image includes selecting said peak intensity value for each pixel of said second combined peak display image from amongst said additional image frame and the other remaining image frames.

8. A method for producing a combined peak display image wit reduced distortion due to motion of anatomical structures comprising:
 gathering a set of ultrasound image frames;
 storing said set of ultrasound image frames in a memory;
 downloading a plurality of image frames from said memory, wherein said plurality of image frames is less than all of the image frames in said set of ultrasound image frames;
 constructing said combined peak display image by comparing and selecting a peak intensity value for each corresponding pixel from amongst said plurality of image frames for use in constructing said combined peak display image;
 displaying said combined peak display image on a display device.

9. The method of claim 8 further comprising:
 discarding one image frame from said plurality of image frames;
 downloading an additional image frame from said memory and adding said additional image frame to said set of image frames to produce a second set of image frames; and
 constructing a combined second peak display image from said second set of image frames.

10. The method of claim 8 wherein said displaying step includes displaying said combined peak display image in a first portion of a monitor and displaying said second combined peak display image in a second portion of said monitor, said monitor being part of said display device.

11. A system for producing a combined peak display image with reduced distortion due to motion of anatomical structures including:
 a transducer emitting ultrasound waves and receiving ultrasonic echoes, wherein said ultrasonic echoes are converted into data;
 an image frame processing unit receiving said data from said transducer and converting said data into image frames;
 a combined peak display image processing unit receiving said image frames and constructing said combined peak display images, wherein said combined peak display image processing unit accumulates said image frames into a set of image frames spanning an accumulation interval, compares corresponding pixels from said image frames in said set of image frames, selects a pixel with a peak intensity value for each said corresponding pixel from amongst said set of image frames, and constructs said combined peak display image using said pixel with said peak intensity value from amongst set of image frames; and
 a display for receiving said combined peak display images and displaying said combined peak display images.

12. The system of claim 11 wherein said combined peak display image processing unit:
 discards an image frame from said set of image frames and adds a new image frame to create another set of image frames.

13. The system of claim 12 wherein said combined peak display image processing unit:
 constructs a second combined peak display image using said another set of image frames.

14. The system of claim 11 wherein said accumulation interval is a predetermined number of image frames.

15. The system of claim 14 wherein a user inputs said predetermined number of image frames.

16. The system of claim 11 wherein said accumulation interval is a predetermined period of time.

17. The system of claim 16 wherein a user inputs said predetermined period of time.

18. The system of claim 16 wherein said predetermined period of time is converted to a number of image frames.

* * * * *

UNITED STATES PATENT AND TRADEMARK OFFICE
CERTIFICATE OF CORRECTION

PATENT NO. : 7,583,828 B2 Page 1 of 1
APPLICATION NO. : 10/920813
DATED : September 1, 2009
INVENTOR(S) : Hall et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 948 days.

Signed and Sealed this

Fourteenth Day of September, 2010

David J. Kappos
*Director of the United States Patent and Trademark Office*